US010743780B2

(12) United States Patent
Hoem et al.

(10) Patent No.: US 10,743,780 B2
(45) Date of Patent: Aug. 18, 2020

(54) CATHETER SYSTEM AND METHOD FOR OCCLUDING A BODY VESSEL

(75) Inventors: Jon H. Hoem, Oberaegeri (CH); Oliver A. Kohr, Unteraegeri (CH)

(73) Assignee: Miracor Medical SA, Vienna ( * ) Notice: Subject to any disclaimer, the term of this patent is extended or adjusted under 35 U.S.C. 154(b) by 598 days.

(21) Appl. No.: 12/786,743

(22) Filed: May 25, 2010

(65) Prior Publication Data

US 2011/0295301 A1 Dec. 1, 2011

(51) Int. Cl.
*A61M 29/00* (2006.01)
*A61B 5/0215* (2006.01)
(Continued)

(52) U.S. Cl.
CPC ....... *A61B 5/0215* (2013.01); *A61M 25/0032* (2013.01); *A61M 25/10* (2013.01);
(Continued)

(58) Field of Classification Search
CPC .......... A61M 25/0053; A61M 25/0054; A61M 2025/0063; A61M 25/10; A61M 25/001; A61M 25/0012; A61M 25/0013; A61M 25/0015; A61M 25/0045; A61M 25/0052; A61M 25/0067; A61M 25/0068; A61M 25/007; A61M 25/0071; A61M 25/008; A61M 2025/1093; A61M 2025/1095; A61M 2025/1097; A61M 2210/125; A61M 25/0141; A61M 25/0144; A61M 25/0152; A61M 25/0051; A61M 25/005; A61M 25/0102; A61M 25/0138; A61M 25/0032;
(Continued)

(56) References Cited

U.S. PATENT DOCUMENTS

| 1,611,914 A | 12/1926 | Jenkins |
| 3,995,623 A | 12/1976 | Blake et al. |

(Continued)

FOREIGN PATENT DOCUMENTS

| EP | 1611914 A1 * | 1/2006 | ............ A61M 25/00 |
| UA | 14911 U | 6/2006 | |

(Continued)

OTHER PUBLICATIONS

'Letters to the Editor: A New Technique for Pulmonary Arterial Catheter Insertion into Coronary Sinus Using Transesophageal Echocardiography' [online]. International Anesthesia Research Society, 2003 [retrieved May 27, 2010]. Retrieved from the Internet: <URL: http://www.anesthesia-analgesia.org/content/97/1/298.full.pdf>.

(Continued)

*Primary Examiner* — Darwin P Erezo
*Assistant Examiner* — Erin L Colello
(74) *Attorney, Agent, or Firm* — Fish & Richardson P.C.

(57) ABSTRACT

Some embodiments of a balloon catheter device for introduction into a body vessel, in particular the coronary sinus, can include a catheter shaft which carries an inflatable balloon on its distal portion and in which a plurality of different lumens are formed. In particular embodiments, a system for treating heart tissue can include a coronary sinus occlusion catheter configured for improved deliverability to the coronary sinus and for thereafter performing intermittent occlusion of the coronary sinus.

10 Claims, 5 Drawing Sheets

(51) Int. Cl.
*A61M 25/00* (2006.01)
*A61M 25/10* (2013.01)

(52) U.S. Cl.
CPC ....... *A61M 25/007* (2013.01); *A61M 25/0054* (2013.01); *A61M 25/0069* (2013.01); *A61M 25/10184* (2013.11); *A61M 25/10188* (2013.11); *A61M 2025/0003* (2013.01); *A61M 2025/0063* (2013.01); *A61M 2025/1052* (2013.01); *A61M 2025/1093* (2013.01)

(58) Field of Classification Search
CPC ...... A61M 25/10184; A61M 25/10188; A61M 25/0069; A61M 25/0029; A61M 25/003; A61M 2025/0001; A61M 2025/0002; A61M 2025/0003; A61M 2025/0004; A61M 2025/1052; A61B 17/12109; A61B 17/1204; A61B 17/12122; A61B 17/12136; A61B 2017/00292; A61B 2017/003; A61B 2017/00305; A61B 2017/00309; A61B 2017/00331; A61B 5/0215
USPC ....... 606/191, 192, 193, 194, 196, 197, 198; 604/96.01, 99.01, 100.01, 100.03, 104; 600/16, 17
See application file for complete search history.

(56) References Cited

U.S. PATENT DOCUMENTS

| | | | |
|---|---|---|---|
| 4,546,759 A * | 10/1985 | Solar | A61M 1/1072 600/18 |
| 4,589,869 A | 5/1986 | Wernborg | |
| 4,657,536 A | 4/1987 | Dorman | |
| 4,670,009 A * | 6/1987 | Bullock | 604/533 |
| 4,671,796 A | 6/1987 | Groshong et al. | |
| 4,701,166 A | 10/1987 | Groshong et al. | |
| 4,705,501 A | 11/1987 | Wigness et al. | |
| 4,887,608 A * | 12/1989 | Mohl et al. | 600/486 |
| 4,931,036 A * | 6/1990 | Kanai | A61M 1/1072 600/18 |
| 4,934,996 A * | 6/1990 | Mohl et al. | 600/17 |
| 4,943,277 A | 7/1990 | Bolling | |
| 4,969,470 A * | 11/1990 | Mohl et al. | 600/486 |
| 5,021,045 A * | 6/1991 | Buckberg | A61M 25/1002 604/101.04 |
| 5,024,668 A * | 6/1991 | Peters et al. | 606/194 |
| 5,033,998 A * | 7/1991 | Corday | A61M 25/1002 600/18 |
| 5,141,518 A * | 8/1992 | Hess | A61M 25/104 604/913 |
| 5,156,600 A | 10/1992 | Young | |
| 5,224,938 A | 7/1993 | Fenton, Jr. | |
| 5,226,427 A * | 7/1993 | Buckberg | A61M 25/1002 600/585 |
| 5,324,253 A * | 6/1994 | McRea et al. | 604/8 |
| 5,324,260 A * | 6/1994 | O'Neill et al. | 604/103.08 |
| 5,328,472 A * | 7/1994 | Steinke | A61M 25/104 604/102.02 |
| 5,342,303 A * | 8/1994 | Ghaerzadeh | A61M 25/10 604/102.01 |
| 5,370,640 A * | 12/1994 | Kolff | 606/2 |
| 5,456,665 A | 10/1995 | Postell et al. | |
| 5,458,574 A * | 10/1995 | Machold et al. | 604/101.03 |
| 5,466,216 A | 11/1995 | Brown et al. | |
| 5,505,698 A * | 4/1996 | Booth et al. | 604/103.11 |
| 5,551,439 A * | 9/1996 | Hickey | A61B 5/0215 600/486 |
| 5,599,326 A * | 2/1997 | Carter | 604/524 |
| 5,653,690 A * | 8/1997 | Booth et al. | 604/103.07 |
| 5,683,347 A | 11/1997 | Miyata et al. | |
| 5,707,358 A * | 1/1998 | Wright | A61M 25/1011 604/103.07 |
| 5,779,685 A | 1/1998 | Thompson et al. | |
| 5,716,373 A * | 2/1998 | Wolvek | A61M 1/1072 606/191 |
| 5,755,686 A | 5/1998 | O'Neill et al. | |
| 5,775,327 A * | 7/1998 | Randolph et al. | 600/374 |
| 5,807,328 A * | 9/1998 | Briscoe | A61M 25/0075 604/102.02 |
| 5,911,715 A * | 6/1999 | Berg | A61M 25/0009 138/125 |
| 5,961,510 A * | 10/1999 | Fugoso | A61M 25/0054 604/524 |
| 6,029,671 A * | 2/2000 | Stevens et al. | 128/898 |
| 6,066,114 A * | 5/2000 | Goodin | A61M 25/104 604/103.04 |
| 6,080,170 A * | 6/2000 | Nash | A61B 17/22 606/159 |
| 6,083,215 A * | 7/2000 | Milavetz | 604/509 |
| 6,179,856 B1 * | 1/2001 | Barbere | A61M 25/1006 604/97.02 |
| 6,475,209 B1 * | 11/2002 | Larson et al. | 604/525 |
| 6,500,145 B1 * | 12/2002 | Bicakci | A61M 25/10 604/96.01 |
| 6,506,146 B1 | 1/2003 | Mohl et al. | |
| 6,508,777 B1 * | 1/2003 | Macoviak et al. | 604/4.01 |
| 6,569,145 B1 | 5/2003 | Shmulewitz et al. | |
| 6,629,952 B1 * | 10/2003 | Chien et al. | 604/103.09 |
| 6,652,546 B1 * | 11/2003 | Nash et al. | 606/159 |
| 6,673,040 B1 * | 1/2004 | Samson et al. | 604/101.01 |
| 6,682,499 B2 * | 1/2004 | Lenker | A61M 1/3653 604/4.01 |
| 6,702,802 B1 * | 3/2004 | Hancock | A61F 2/958 604/104 |
| 6,758,854 B1 * | 7/2004 | Butler et al. | 606/194 |
| 6,858,024 B1 * | 2/2005 | Berg et al. | 604/525 |
| 6,953,470 B2 * | 10/2005 | Holman | A61M 25/0054 604/103 |
| 7,166,100 B2 * | 1/2007 | Jordan et al. | 604/525 |
| 7,179,251 B2 * | 2/2007 | Palasis | A61M 25/104 604/101.02 |
| 7,189,215 B2 * | 3/2007 | Murray, III | 604/103.09 |
| 7,331,922 B2 * | 2/2008 | Mohl | 600/17 |
| 7,815,600 B2 * | 10/2010 | Al-Marashi et al. | 604/103.04 |
| 8,348,889 B2 * | 1/2013 | Salemi et al. | 604/101.01 |
| 8,626,316 B2 * | 1/2014 | Mohl | A61B 5/0215 604/96.01 |
| 9,023,010 B2 * | 5/2015 | Chiu et al. | 604/509 |
| 9,033,896 B2 * | 5/2015 | Lerman | A61B 10/06 600/564 |
| 2001/0053920 A1 * | 12/2001 | Shaker | A61B 5/037 606/197 |
| 2002/0072730 A1 * | 6/2002 | McGill et al. | 604/525 |
| 2002/0120232 A1 | 8/2002 | Stumpp et al. | |
| 2003/0032974 A1 * | 2/2003 | Leschinsky | A61M 1/1072 606/192 |
| 2004/0172004 A1 | 9/2004 | Mohl | |
| 2004/0181206 A1 * | 9/2004 | Chiu et al. | 604/509 |
| 2005/0015048 A1 * | 1/2005 | Chiu et al. | 604/101.04 |
| 2005/0070880 A1 * | 3/2005 | Varma | A61M 25/0023 604/524 |
| 2006/0074399 A1 * | 4/2006 | Bates | 604/522 |
| 2006/0200047 A1 * | 9/2006 | Galdonik et al. | 600/585 |
| 2006/0258987 A1 * | 11/2006 | Lentz et al. | 604/164.01 |
| 2007/0060883 A1 * | 3/2007 | Doty | 604/103.04 |
| 2007/0083126 A1 * | 4/2007 | Marko et al. | 600/505 |
| 2007/0088257 A1 * | 4/2007 | Fisher | A61M 25/10 604/103.04 |
| 2007/0135763 A1 * | 6/2007 | Musbach | A61M 25/0054 604/96.01 |
| 2008/0015404 A1 | 1/2008 | Mohl | |
| 2008/0103478 A1 * | 5/2008 | Chiu et al. | 604/509 |
| 2008/0119742 A1 * | 5/2008 | Mohl | 600/486 |
| 2010/0056849 A1 | 3/2010 | Mohl | |

(56) References Cited

U.S. PATENT DOCUMENTS

2010/0130810 A1    5/2010  Mohl
2010/0256506 A1*  10/2010  Mohl ........................... 600/486

FOREIGN PATENT DOCUMENTS

WO     WO 89/10155     11/1989
WO     WO 03/041783     5/2003

OTHER PUBLICATIONS

'Global Myocardial Protection' [online]. Edwards Lifesciences, 2004 [retrieved May 27, 2010]. Retrieved from the Internet: <URL: http://ht.edwards.com/resourcegallery/products/cannulae/images/ar00519.pdf>.

'Myocardial Protection System' [online]. Quest Medical, Inc. 2010 [retrieved May 27, 2010]. Retrieved from the Internet: <URL: http://www.questmedical.com/products/mps.asp>.

'Cardioplegia Delivery' [online]. Quest Medical, Inc. 2010 [retrieved May 27, 2010]. Retrieved from the Internet: <URL: http://www.questmedical.com/products/cardio_catheters.asp>.

'Cannulation' [online]. Medtronic, Inc. 2010 [retrieved May 27, 2010]. Retrieved from the Internet: <URL: http://www.medtronic.com/for-healthcase-professionals/products-therapies/cardiovascular/therapies/cannulation/index.htm>.

'MiRCSP Cannulae' [online]. Medtronic, Inc. 2010 [retrieved May 27, 2010]. Retrieved from the Internet: <URL: http://www.medtronic.com/for-healthcare-professionals/products-therapies/cardiovascular/cannulae-products/mircsp-cannula/index.htm>.

'Retrograde Perfusion Cannulae' [online]. Medtronic, Inc. 2010 [retrieved May 27, 2010]. Retrieved from the Internet: <URL: http://www.medtronic.com/for-healthcare-professionals/products-therapies/cardiovascular/cannulae-products/retrograde-perfusion-cannulae/index.htm>.

'Performer CPB' [online]. Medtronic, Inc. 2007 [retrieved May 27, 2010]. Retrieved from the Internet: <URL: http://www.medtronic.com/cardsurgery/arrested_heart/downloads/200704933.pdf>.

Mohl, Werner et al., "The legacy of coronary sinus interventions: Endogenous cardioprotection and regeneration beyond stem cell research." The American Association for Thoracic Surgery, 2008. The Journal of Thoracic and Cardiovascular Surgery, vol. 136, No. 5, pp. 1131-1135.

Mohl, Werner et al., "Is activation of coronary venous cells the key to cardiac regeneration?" Macmillan Publishers Ltd., 2008. Nature Clinical Practice, Cardiovascular Medicine, vol. 5, No. 9, pp. 528-530.

Onorati et al., "Coronary Sinus Perfusion Reverses Ongoing Myocardial Damage in Acute Ischemia." Wiley Periodicals, Inc. 2009. Journal compilation, International Center for Artificial Organs and Transplantation and Wiley Periodicals, Inc., 33 (10), pp. 788-797.

Mohl, Werner et al. "Coronary Sinus Library, ICSO and PICSO" Society of Coronary Sinus Interventions, 2003. A. Holzhausens Nfg., Austria.

European Search Report for Application No. 10 45 0091, dated Nov. 5, 2010, 3 pages.

Mohl et al., "Intermitten Pressure Elevation of the Coronary Venous System as a Method to Protect Ischemic Myocardium," *Interactive CardioVascular and Thoracic Surgery*, vol. 4, 2005, pp. 66-69.

Syeda et al., "The Salvage Potential of Coronary Sinus Interventions: Meta-Analysis and Pathophysiologic Consequences," *The Journal of Thoracic and Cardiovascular Surgery*, vol. 127, No. 6 (Jun. 2004), pp. 1703-1712.

\* cited by examiner

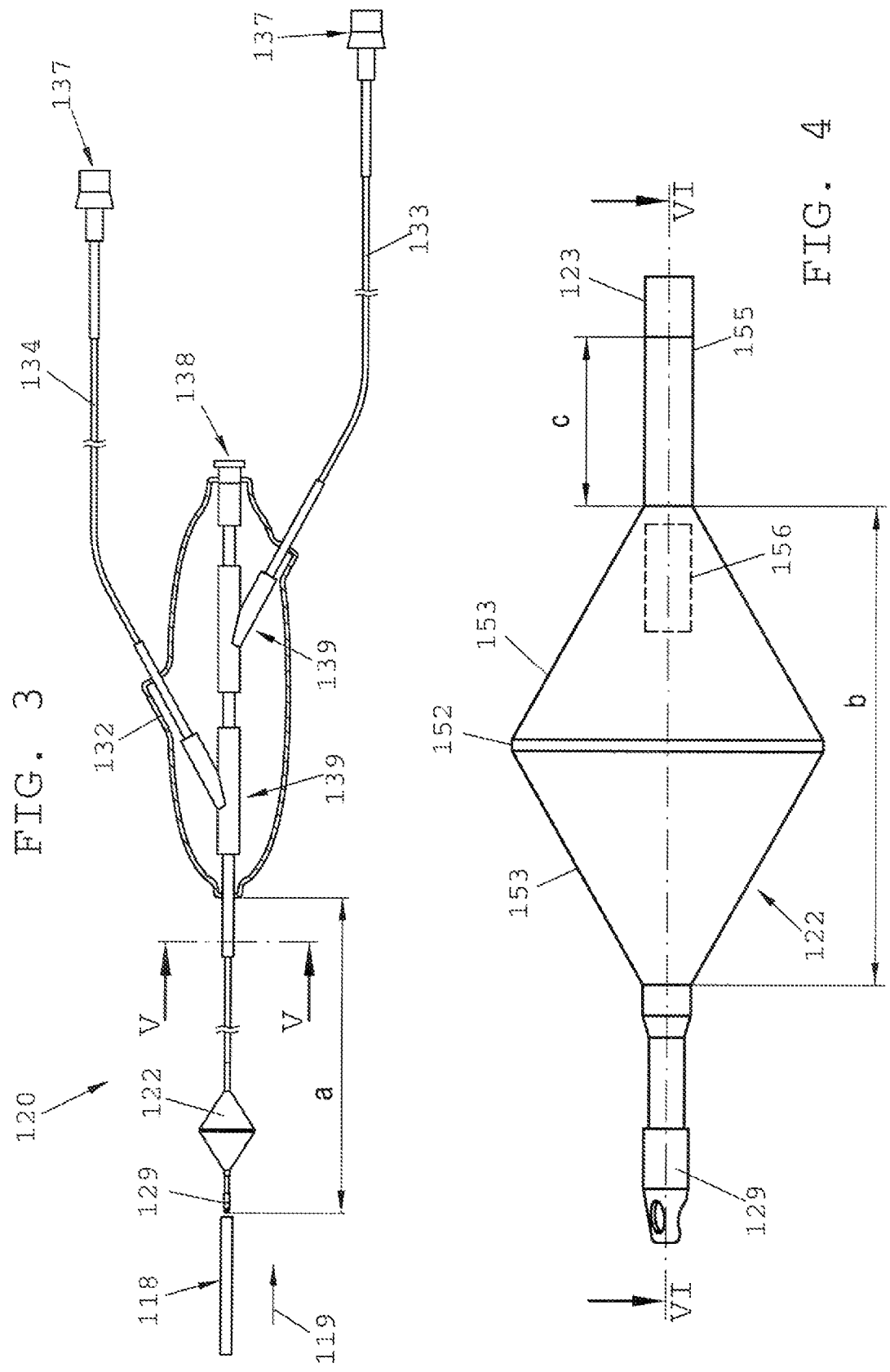

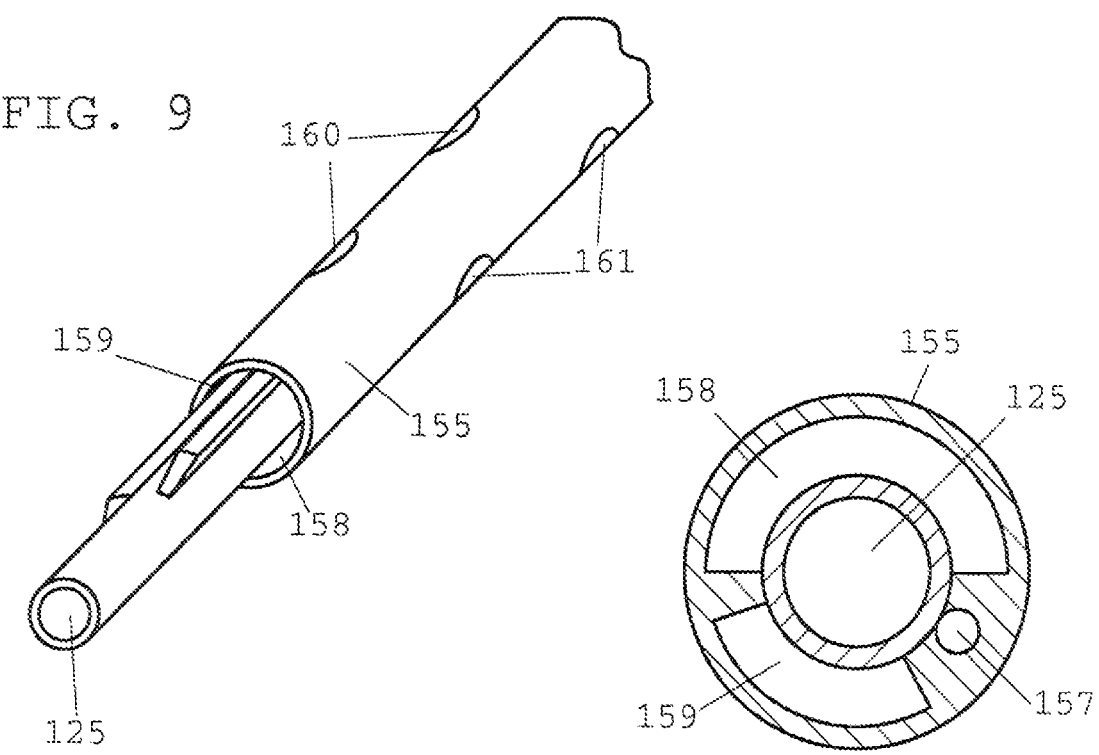
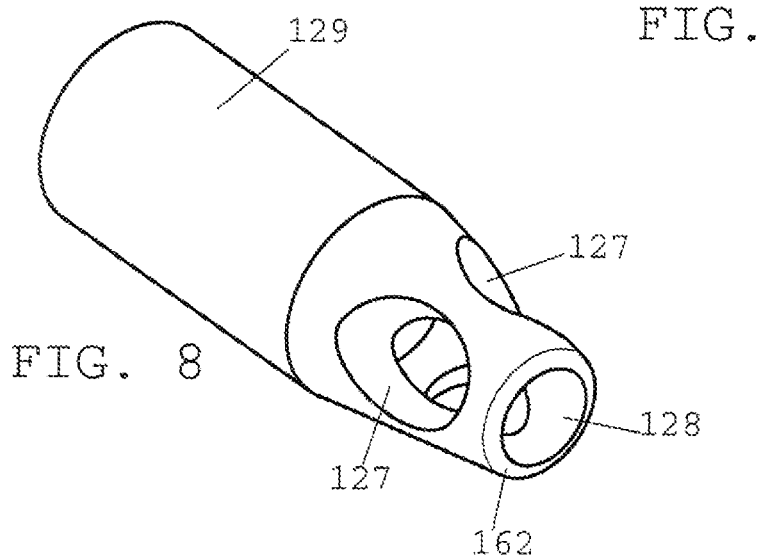
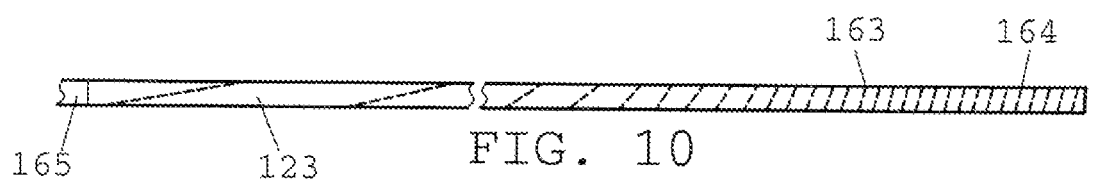

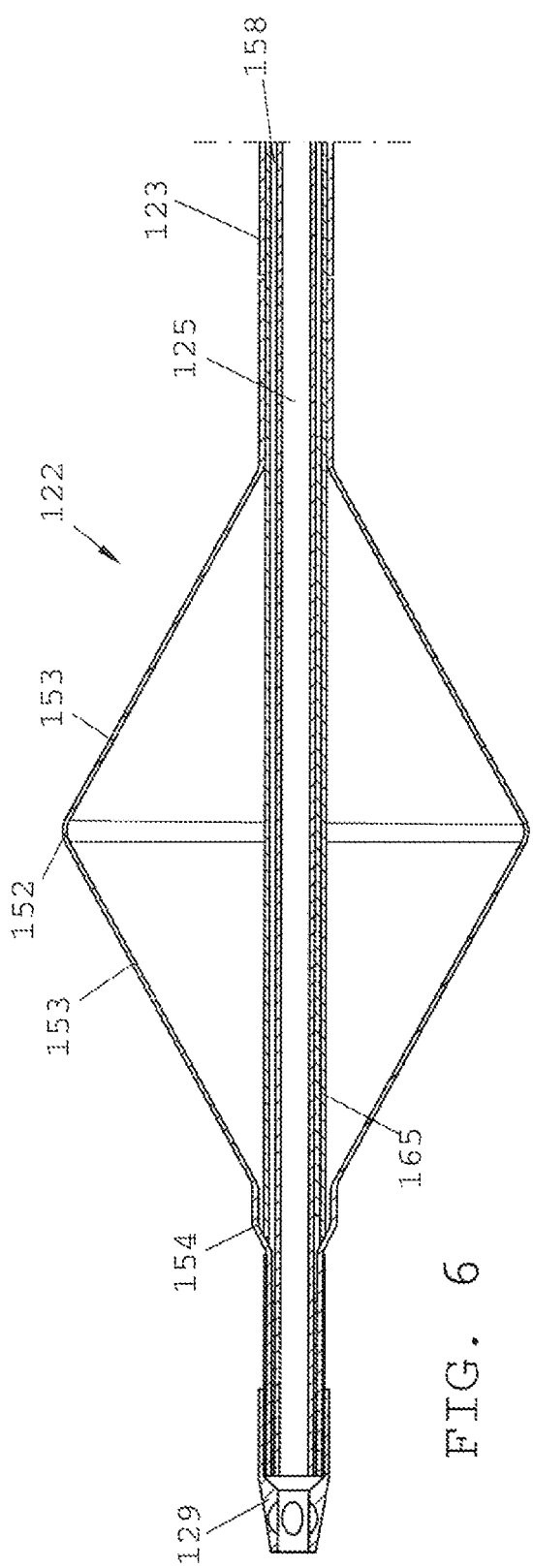
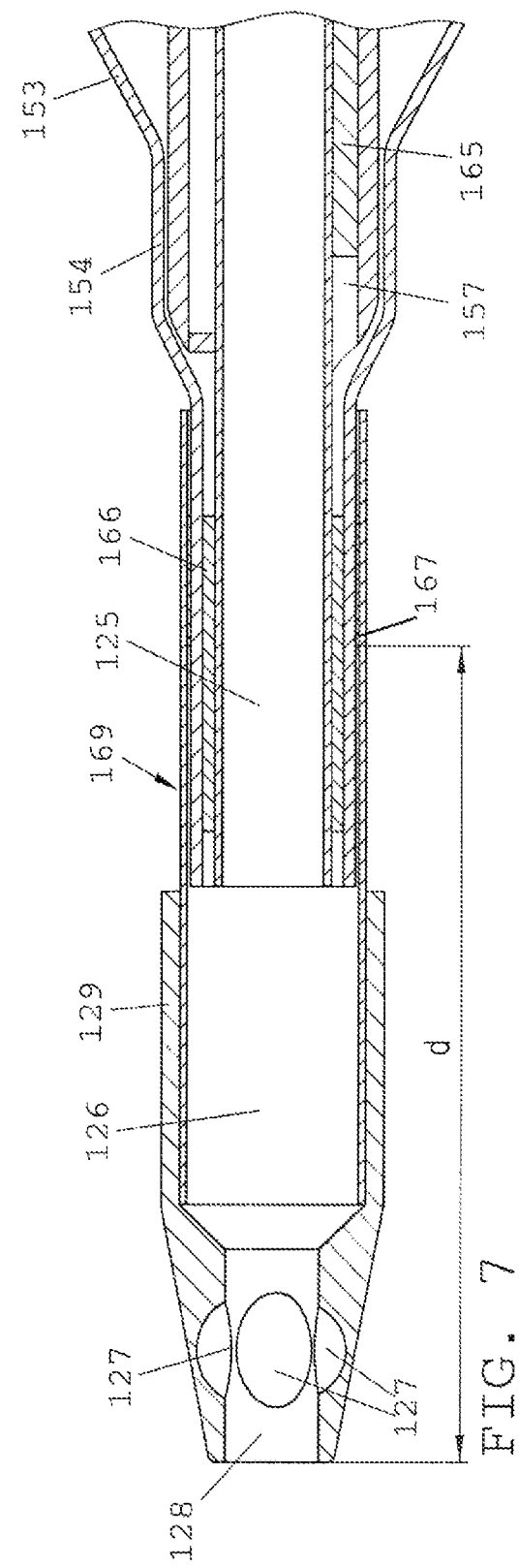
FIG. 6
FIG. 7

CATHETER SYSTEM AND METHOD FOR OCCLUDING A BODY VESSEL

TECHNICAL FIELD

This document relates to a balloon catheter for introduction into a body vessel, such as the coronary sinus, and the occlusion of the same, including a catheter shaft which carries an inflatable balloon on its distal end portion and in which a plurality of lumens are formed.

BACKGROUND

Balloon catheters including inflatable balloons can, for instance, be taken from EP 402964 B1. The known balloon catheter serves for coronary sinus occlusion, wherein diagnostically valuable signals can be obtained by a plurality of sensors and the inflation of the balloon can be controlled, in particular, with a view to achieving retroperfusion. Such a balloon catheter is also known as a multi-lumen catheter, whose distal end projects, for instance, into the coronary sinus of the heart, while the proximal end of the catheter is connected with a pump for inflating the balloon. Wires for electrically contacting sensors can be conducted through further lumens arranged coaxially or in parallel with the lumen that serves to inflate the expandable balloon. Via such further lumens, cardioplegic or thrombolytic, or other pharmacologically active substances suitable for retroperfusion in ischemic tissue, can also be introduced.

In order to supply ischemic tissue with blood by retrograde perfusion, it has already been proposed to use an inflatable balloon fixed to the end of a catheter to intermittently occlude the coronary sinus. The blood pressure in the coronary sinus rises during the occlusion at every heart beat so as to cause blood reaching the coronary sinus through the healthy tissue of the heart muscle to be flushed back into the ischemic tissue. Another effect of intermittent occlusion is the influence on the pressure regulation due to the feedback mechanism by neuro-stimulative effects. For such intermittent coronary sinus occlusion, the balloon end of the catheter is inserted either percutaneously or surgically. The other end of the catheter is supplied by a pump with a gas or fluid which causes the cyclic inflation and deflation of the balloon. A device for the retroperfusion of coronary veins is, for instance, known from WO 2005/120602 A1, by which a pressure-controlled, intermittent coronary sinus occlusion can be performed. In that device and the corresponding method for determining the optimum times for triggering and releasing the occlusion, pressure parameters like the speeds of the pressure increase and pressure drop were determined and subjected to relatively complex processing.

For the percutaneous insertion of a catheter, it is proceeded in a manner that the catheter is guided via the inferior or the superior cava vein into the right atrium of the heart, into which the coronary sinus runs. Due to the position of the mouth of the superior cava vein or inferior cava vein, respectively, relative to the mouth of the coronary sinus, the introduction of the catheter into the coronary sinus requires considerable skill from the cardiologist in order to direct the tip of the catheter, or a guide wire or a guide sleeve, into the coronary sinus in such a manner as to enable the subsequent introduction of the catheter along with the occlusion device. In fact, it frequently happened that several attempts of introduction into the coronary sinus had to be made, which considerably extended the duration of treatment and, hence, the strain on the patient.

Another problem involved in balloon catheters used for the intermittent occlusion of the coronary sinus resides in that blood backed up during the occlusion would exert pressure on the balloon, and hence on the catheter, thus eventually causing the catheter to slip back or kink within the vessel.

SUMMARY

Some systems and methods described herein include an occlusion catheter device that is sufficiently rigid in order to reduce the likelihood the occlusion catheter device will slip back from the occluded position because of the counter-pressure in the occluded vessel. At the same time, the occlusion catheter device may provide sufficient flexibility in order to enable the occlusion catheter device to be safely pushed forward through blood vessel regions having small radii of curvature so as to be able to position an inflatable balloon on the catheter device at the desired site of application (e.g., the coronary sinus in some embodiments).

In particular embodiments, a balloon catheter which is suitable for the intermittent occlusion of a body vessel (e.g., the coronary sinus) can be equipped with the lumens required performing the intermittent occlusion of the body vessel. The balloon catheter can be configured to exhibit both sufficient flexural strength to enhance the pushability of the catheter while also reducing the likelihood that the balloon will not slip back on account of the pressure caused by the backed-up fluid in the occluded vessel, and sufficient flexibility to facilitate its introduction.

In some embodiments, the balloon catheter can include a central lumen having a distal opening in communication with the respective body vessel distally of the balloon. Furthermore, a lumen serving to inflate and deflate the balloon and communicating with the latter is provided. Also, the balloon catheter may include a stiffening element surrounding at least a portion of the catheter shaft, or arranged within at least a portion of the catheter shaft. A distal end portion of the stiffening member, which may be positioned adjacent to the proximal end of the balloon, can have a flexural strength that is reduced relative to the remaining portion of the stiffening element.

The central lumen of the balloon catheter, which includes the distal opening into the respective body vessel distally of the balloon, enables measurement of the pressure prevailing in the body vessel occluded by the balloon (e.g., the coronary sinus pressure in the coronary sinus). In some circumstances, the central lumen also enables the taking of blood from the occluded vessel. Moreover, the central lumen can be used to introduce the balloon catheter into the vessel, and advance it within the vessel to the respectively targeted site, by advancing the central lumen over a guide wire.

In some embodiments, the flexural strength of the balloon catheter is obtained by the stiffening element that surrounds the catheter shaft, or is arranged within the catheter shaft. The stiffening element also facilitates the advancement of the balloon catheter. In order reduce the likelihood of injuring the vessel during the advancement of the catheter, and to permit advancement in curved regions having small radii of curvature, the distal end portion of the stiffening element can be positioned adjacent to the proximal end of the balloon and may provide a flexural strength that is reduced relative to the remaining portion of the stiffening element. Thus, a region of higher flexibility is deliberately formed at the distal end portion of the stiffening element so as to enable the adaptation to a curved course of the body vessel during the advancement of the catheter, while preferably maintaining the balloon-carrying, distal portion of the catheter in a generally parallel relationship with the longitudinal extension of the respective vessel in order to avoid injury to the vessel wall.

In particular embodiments, the stiffening element is preferably formed by a hypotube surrounding the catheter shaft. The stiffening element in this case preferably extends substantially over the entire portion of the catheter shaft between the balloon and the proximal end portion. In a preferred manner, a slight distance is provided between the distal end of the stiffening element and the proximal end of the inflatable region of the balloon. In the embodiment described herein, the distance is dimensioned such that, on the one hand, the catheter shaft will not buckle between the distal end of the stiffening tube and the balloon, which would be the case with too large a distance, and, on the other hand, the flexibility and suppleness will not be limited too much in this region, which would be the case with too short a distance, or no distance at all. In some preferred embodiments, the distance is about 4-6 mm and, in particular, about 5 mm.

In one aspect, the hypotube may be formed by a separate stainless-steel tube or also by at least one outer layer co-extruded with the catheter shaft and made of a synthetic material differing from that of the catheter shaft. Alternatively, the hypotube may be formed by a nylon tissue or comprise such a tissue. In some embodiments, the portion of the stiffening element having a reduced flexural strength extends over a length of about 30-120 mm, preferably about 40-90 mm, from the distal end of the stiffening element.

According to a preferred configuration, the hypotube can include at least one notch influencing the flexural strength. In some embodiments, the notch preferably extends in a helical line-shaped manner, with the helical line or helix having a smaller pitch in the portion of reduced flexural strength of the hypotube than in the remaining portion. As described herein, further optimization is feasible in that the pitch of the helix continuously increases in the portion of reduced flexural strength of the hypotube, departing from the distal end of the hypotube. Due to the continuously variable flexural strength of the hypotube in the mentioned end portion, buckling sites will be avoided.

In alternative embodiments, instead of a helical line-shaped notch, a plurality of notches offset in the axial direction may also be provided on the stiffening element. Each of the notches can extend over a partial circumference of the hypotube, with the flexural strength depending on the axial distance between the individual notches.

For the intermittent occlusion of a body vessel and, in particular, the coronary sinus, a plurality of lumens are usually required such that a particularly space-saving arrangement of the individual lumens is useful in order to maintain the outer diameter of the catheter shaft as small as possible. Accordingly, the lumens of the catheter may have cross-sectional geometries differing from one another. In some embodiments, the inflation lumen that serves to inflate and/or deflate the balloon may have a ring segment-shaped in cross section and arranged radially outside the central lumen.

In some embodiments, a separate lumen in the balloon catheter can be employed to monitor the fluid pressure prevailing in the balloon. In particular embodiments, the balloon pressure-monitoring lumen may have a ring segment-shaped in cross section and arranged radially outside the central lumen, whose arc-determining angle is preferably smaller as compared to the ring segment-shaped inflation lumen serving to inflate and deflate the balloon. Due to the fact that the ring segment-shaped cross section of the inflation lumen extends over a larger central angle than the ring segment-shaped cross section of the balloon pressure-monitoring lumen, a larger cross section is provided for the inflation lumen and, at the same time, separate pressure measurements will be enabled, thus providing a configuration that utilizes the catheter space while maintaining the outer diameter of the catheter shaft accordingly small.

In particular embodiments, the ability for pressure measurement via a separate lumen (e.g., the balloon pressure-monitoring lumen that is separate from the inflation lumen) can provide the advantage that possible buckling under flexural load can be detected. Buckling can be reliably detected due to the different pressures measured in the inflation lumen serving to inflate and deflate the balloon and in the balloon pressure-monitoring lumen. In such circumstances, it is thus feasible to take the respective safety measurements, e.g. actuate a safety valve, in due time.

According to a further preferred configuration, it is provided that a circular or oval lumen is provided between the neighboring ends of the ring segment-shaped lumens. Such a relatively small lumen enables the wiring of electrical sensors arranged in the tip of the catheter or in the region of the balloon, or the arrangement of fiber-optic lines.

In order to avoid possible malfunctions during the inflation and deflation of the balloon, it is provided according to a preferred further development that the inflation lumen, and optionally the balloon pressure-monitoring lumen, are each connected with the interior of the balloon via at least two radial openings arranged to be offset in the axial direction of the catheter. The use of at least two radial openings into the interior of the balloon can reduce the risk of the balloon prematurely covering all openings, particularly during collapsing, i.e. prior to the complete evacuation of the balloon, so that further evacuation would be rendered difficult or impossible.

In some embodiments, the balloon catheter may include a stiffening means, such as a stiffening wire, in the region of the balloon. The stiffening wire may extend over the length of the balloon, and may extend from a region interior to the previously describe hypotube to a distal region interior to a distal collar of the balloon. Such a stiffening means can reduce the likelihood of the catheter shaft buckling or otherwise deforming in the region in which it is surrounded by the balloon, on account of the balloon pressure exerting axial upsetting forces on the catheter shaft. The stiffening means can, for instance, be received in the circular or oval lumen mentioned above. In an alternative embodiment, the stiffening wire may be arranged in a helical wrap around an outer circumference of the catheter shaft in the interior region of the balloon.

In particular embodiments, the distal end of the catheter can be connected with a catheter tip element which comprises an axial lumen provided consecutively to the central lumen of the catheter and having a distal opening, the wall of said axial lumen including at least two, preferably three, radial openings uniformly distributed over its periphery. Such a separate catheter tip component offers various advantages in terms of application. Thus, the edge of the distal opening of the catheter tip element may, for instance, be rounded off so as to prevent damage to the vessel walls. Furthermore, the catheter tip element may conically taper toward the distal opening, and the catheter tip element may, in particular, be designed to be flexible in order to ensure an enhanced guidance of the tip, and hence the overall catheter, within the body vessel. In this respect, the catheter tip element should have a minimum length in order to provide an appropriate bending zone. In a preferred manner, the distance between the distal tip of the catheter tip element and the distal end of the balloon is at least about 30 mm and, preferably, about 35 mm to about 45 mm.

By the axial lumen of the catheter tip element communicating with the body vessel not only via the distal opening of the catheter tip element, but also via at least two, preferably three, radial openings uniformly distributed over its periphery in the wall of the catheter tip element, a more precise measurement of the fluid pressure prevailing in the body vessel has become feasible. In particular, the likelihood of faulty measurements can be reduced because the radial openings can properly measure the fluid pressure in the body vessel eve if the distal opening or one radial opening were in abutment with the vessel wall, or if one opening was not powered with the full pressure prevailing in the vessel for any other reason.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3 is a schematic illustration of a catheter device of the system of FIG. 1.

FIG. 4 is a detailed view of the balloon of the catheter device of FIG. 3.

FIG. 5 shows a cross sectional view of the catheter device of FIG. 3.

FIG. 6 shows a cross sectional view of a portion of the catheter device of FIG. 4.

FIG. 7 is a cross-sectional view of a catheter tip element of the catheter device of FIG. 3.

FIG. 8 is a perspective view of the catheter tip element of FIG. 7.

FIG. 9 is a detailed view of a portion of the catheter of FIG. 3 with the balloon removed from the view.

FIG. 10 is a detail view of a stiffening element for the catheter of FIG. 3.

Like reference symbols in the various drawings indicate like elements.

DETAILED DESCRIPTION

Figure 1:
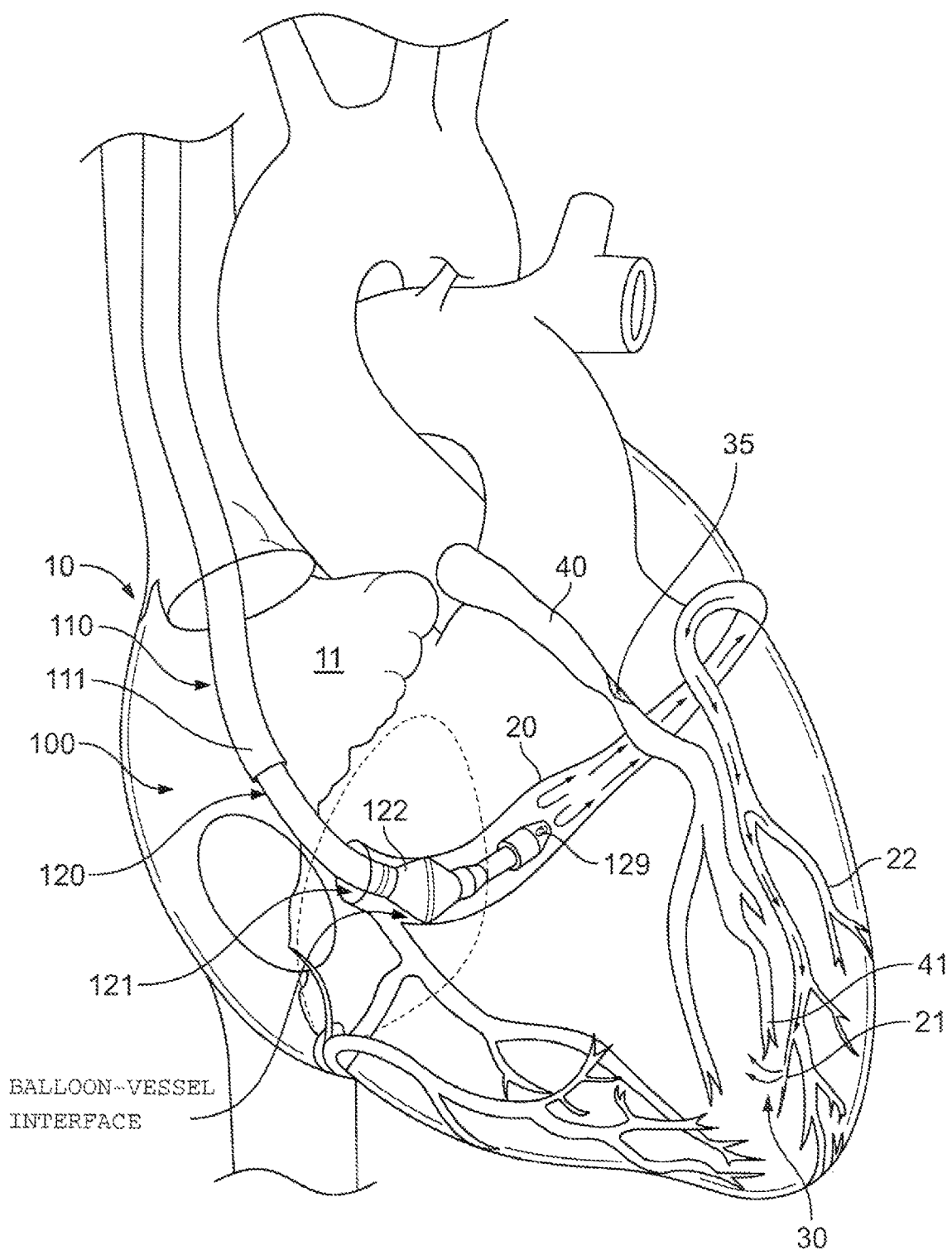
FIG. 1 is a perspective view of a portion of a system for treating heart tissue, in accordance with some embodiments.
Figure 2:
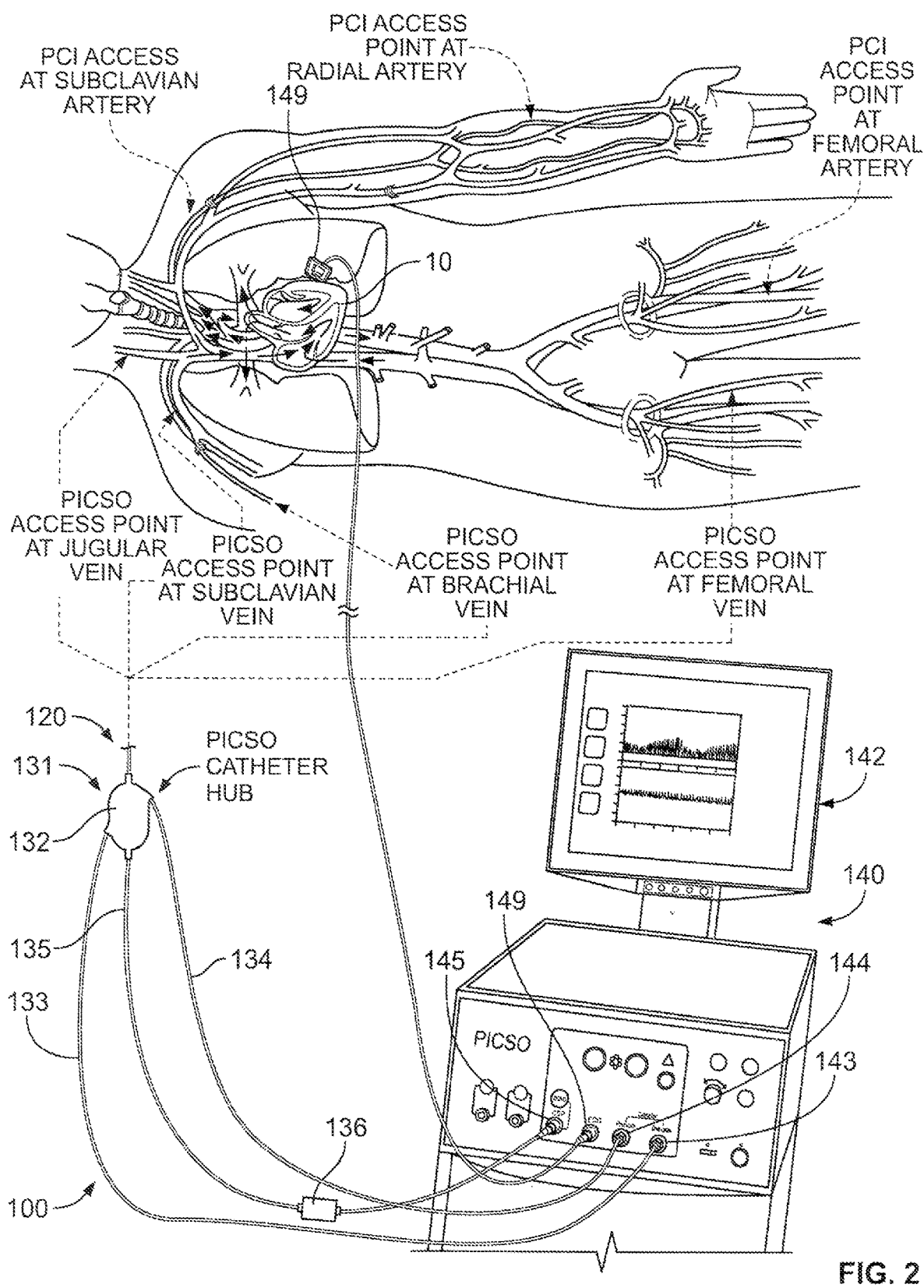
FIG. 2 is a perspective view of another portion of the system of FIG. 1.

Referring to FIGS. 1-2, some embodiments of a system 100 for treating heart tissue can include a coronary sinus occlusion catheter 120 and a control system 140 (FIG. 2). In particular embodiments, the control system 140 can be configured to control the operation of the catheter 120 for providing pressure-controlled intermittent coronary sinus occlusion (PICSO) and to receive heart sensor data for display. The coronary sinus occlusion catheter 120 includes a distal tip portion 121 (leading to a distal end depicted in FIG. 1) and a proximal portion 131, which includes a proximal hub 132 that is coupled to the control system 140 via a number of fluid or sensor lines 133, 134, and 135. Accordingly, the control system 140 may be employed to operate one or more components at the distal tip portion 121 of the coronary sinus occlusion catheter 120 while also receiving one or more sensor signals that provide data indicative of heart characteristics (e.g., coronary sinus pressure, electrocardiogram (ECG) information, and the like).

Briefly, in use, the distal tip portion 121 of the coronary sinus occlusion catheter 120 can be arranged in a coronary sinus 20 of a heart 10 and thereafter activated to intermittently occlude the blood flow exiting from the coronary sinus 20 and into the right atrium 11. During such an occlusion of the coronary sinus 20, the venous blood flow that is normally exiting from the coronary sinus 20 may be redistributed into a portion of heart muscle tissue 30 that has been damaged due to blood deprivation. For example, the portion of heart muscle tissue 30 can suffer from a lack of blood flow due to a blockage 35 in a coronary artery 40. As a result, the arterial blood flow to the affected heart muscle tissue 30 via a local artery 41 can be substantially reduced such that the heart muscle tissue 30 becomes ischemic or otherwise damaged. Further, because the arterial blood flow is reduced, the venous blood flow exiting from the local vein 21 is likewise reduced. Other branch veins 22 located at different regions along the heart 10 may continue to receive blood flow, thereby creating a supply of venous blood flow exiting through the coronary sinus 20. In some embodiments, the coronary sinus occlusion catheter 120 can be delivered into the coronary sinus 20 and thereafter activated so as to intermittently occlude the coronary sinus 20 before, during, or after treating the blockage 35 on the arterial side. Such an occlusion can cause the venous blood flow to be redistributed to the local vein 21 and then into the portion of heart muscle tissue 30 can suffer from a lack of blood flow due to a blockage 35 in a coronary artery 40. As such, the ischemic or otherwise damaged heart muscle tissue 30 can be treated with the redistributed venous blood flow in that the heart muscle tissue 30 receives redistribution of flow before, during, and after the blockage 35 is repaired or removed to restore normal coronary arterial blood flow.

Furthermore, in use, the control system 140 (FIG. 2) is configured to provide automated control of an occlusion component (e.g., an inflatable balloon 122 or the like) of the coronary sinus occlusion catheter 120. As described in more detail below, the control system 140 includes a computer processor that executes computer-readable instructions stored on a computer memory device so as to activate or deactivate the occlusion in the coronary sinus 20 in accordance with particular patterns. For instance, the control system 140 can be configured to activate the occlusion component of the catheter 120 in the coronary sinus 20 as part of a predetermined pattern of occlusion periods and release periods that is independent of the coronary sinus pressure, or as part of a pressure-dependent pattern that is at least partially defined by the coronary sinus pressure readings during the procedure. In addition, the control system 120 is equipped with a display device 142 having a graphical user interface that provides a cardiologist or other user with time-sensitive, relevant data indicative of the progress of a coronary sinus occlusion procedure and the condition of the heart 10. As such, the user can readily monitor the patient's condition and the effects of intermittently occluding the coronary sinus 20 by viewing the graphical user interface while contemporaneously handling the coronary sinus occlusion catheter 120 other heart treatment instruments (e.g., angioplasty catheters, stent delivery instruments, or the like). It should be understood from the description herein that, in some embodiments, the control system 140 and the coronary sinus occlusion catheter 120 can be used as part of a system for treating the heart muscle tissue before, during, and after the blockage 35 is repaired or removed to restore normal coronary arterial blood flow.

Referring in more detail to FIG. 1, the coronary sinus occlusion catheter 120 can be delivered via the venous system to the coronary sinus 20 before, during, or after repairing or treating the blockage 35 the coronary artery 40. In such circumstances, the portion of heart muscle tissue 30 that is damaged due to lack of arterial blood flow (as a result of the blockage) can be treated with a supply of venous blood while the normal arterial blood flow is restored (as a result of repairing or removing the blockage 35).

The system 100 may include a guide member 110 that is advanced through the venous system of the patient and into the right atrium 11. The guide member 110 in this embodiment comprises a guide sheath having a lumen extending between a distal end 111 (FIG. 1) and a proximal end. In alternative embodiments, the guide member 110 can include a guide wire having an exterior surface extending between the distal end and the proximal end. Optionally, the guide member 110 includes a steerable mechanism to control the orientation of the distal end so as to steer the distal end 111 through the venous system and into the right atrium 11. Also, the guide member 110 can include one or more marker bands along the distal end 111 so that the position of the distal end can be monitored during advancement using an imaging device.

After the guide member 110 is advanced into the right atrium 11, the distal end 111 may be temporarily positioned in the coronary sinus 20. From there, the distal tip portion 121 of the coronary sinus occlusion catheter 120 can be slidably advanced along the guide member 110 for positioning inside the coronary sinus 20. In the embodiments in which the guide member 110 comprises a guide sheath, the distal tip portion 121 of the coronary sinus occlusion catheter 120 can slidably engage with an interior surface of the lumen during advancement toward the coronary sinus 20. In the alternative embodiments in which the guide member 110 comprises a guide wire structure, the distal tip portion 121 of the coronary sinus occlusion catheter 120 can slidably advance over the exterior surface of the guide wire (e.g., a lumen of the catheter 120 passes over the guide wire) during advancement toward the coronary sinus 20. After the coronary sinus occlusion catheter 120 reaches the coronary sinus 20, the distal end 111 of the guide member 110 can be withdrawn from the coronary sinus 20 and remain in the right atrium 11 during use of the coronary sinus occlusion catheter 120.

Still referring to FIG. 1, the distal tip portion 121 of the coronary sinus occlusion catheter 120 that is positioned in the coronary sinus 20 includes an occlusion component 122, which in this embodiment is in the form of an inflatable balloon device. The occlusion component 122 can be activated so as to occlude the coronary sinus 20 and thereby cause redistribution of the venous blood into the heart muscle tissue 30 that is damaged due to a lack of arterial blood flow. As described in more detail below, the inflatable balloon device 122 can be in fluid communication with an internal lumen of the coronary sinus occlusion catheter 120, which is in turn in communication with a pneumatic subsystem of the control system 140 (FIG. 2). As such, the control system 140 can be employed to expand or deflate the balloon device 122 in the coronary sinus.

The distal tip portion 121 also includes a tip element 129 having one or more distal ports 127 (FIGS. 7-8) positioned distally forward of the inflatable balloon device 122. In the depicted embodiments, the distal ports 127 of the tip element 129 face is a generally radially outward direction and are substantially uniformly spaced apart from one another along the circumference of the distal tip. As described in more detail below, the distal ports 127 of the tip element 129 may all be in fluid communication with a single pressure sensor lumen 125 extending through the coronary sinus occlusion catheter 120. Accordingly, the coronary sinus pressure can be monitored via a pressure sensor device that is in fluid communication with the distal ports 127 of the tip element 129.

Referring now to FIG. 2, the proximal portion 131 of the coronary sinus occlusion catheter 120 and the control system 140 are positioned external to the patient while the distal tip portion 121 is advanced into the coronary sinus 20. The proximal portion 131 includes the proximal hub 132 that is coupled to the control system 140 via a set of fluid or sensor lines 133, 134, and 135. As such, the control system 140 can activate or deactivate the occlusion component 122 at the distal tip portion 121 of the coronary sinus occlusion catheter 120 while also receiving one or more sensor signals that provide data indicative of heart characteristics (e.g., coronary sinus pressure, electrocardiogram (ECG) information, and the like).

The proximal hub 132 of the coronary sinus occlusion catheter 120 serves to connect the plurality of fluid or sensor lines 133, 134, and 135 with the portion of the coronary sinus occlusion catheter 120 that extends into the patient's venous system. For example, the first line 133 extending between the control system 140 and the proximal hub 132 comprises a fluid line through which pressurized fluid (e.g., helium, another gas, or a stable liquid) can be delivered to activate the occlusion component (e.g., to inflate the inflatable balloon device 122). The fluid line 133 is connected to a corresponding port 143 of the control system 140 (e.g., the drive lumen port in this embodiment) so that the line 133 is in fluid communication with a pneumatic control subsystem housed in the control system 140. The proximal hub 132 joins the first line 133 with an inflation lumen 158 (FIG. 5) extending through the coronary sinus occlusion catheter 120 and to the inflatable balloon device 122.

In another example, the second line 134 extending between the control system 140 and the proximal hub 132 comprises a balloon sensor line that is in fluid communication with the interior of the inflatable balloon device 122 so as to measure the fluid pressure within the balloon device 122. The proximal hub 132 joins the second line 134 with a balloon pressure-monitoring lumen 159 (FIG. 5) extending through the coronary sinus occlusion catheter 120 and to the inflatable balloon device 122. The pressure of the balloon device 122 may be monitored an internal control circuit of the control system 140 as part of a safety feature that is employed to protect the coronary sinus 20 from an overly pressurized balloon device 122. The balloon sensor line 134 is connected to a corresponding port 144 of the control system 140 so that a pressure sensor arranged within the control system 140 can detect the fluid pressure in the balloon device 122. Alternatively, the pressure sensor may be arranged in the distal tip portion 121 (e.g., internal to the balloon device 122) or the in the proximal hub 132 such that only a sensor wire connects to the corresponding port 144 of the control system 140.

The proximal hub 132 also connects with a third line 135 extending from the control system 140. The third line 135 comprises a coronary sinus pressure line that is used to measure the fluid pressure in the coronary sinus both when the balloon device 122 is inflated and when it is deflated. The proximal hub 132 joins the third line 135 with a pressure sensor lumen 125 (FIG. 5) extending through the coronary sinus occlusion catheter 120 and to the distal ports 129 that are forward of the balloon device 122. As such, the pressure sensor lumen 125 can be a coronary sinus pressure lumen, with at least a portion of the third line 135 may operating as a fluid-filled path (e.g., saline, another biocompatible liquid, or a combination thereof) that transfers the blood pressure in the coronary sinus 20 to pressure sensor device 136 along a proximal portion of the third line 135. The pressure sensor device 136 samples the pressure measurements (which are indicative of the coronary sinus pressure) and outputs an sensor signal indicative of the coronary sinus pressure to the corresponding port 145 of the control system 140 for input to an internal control circuit (which may include one or more processors that execute instructions stored on one or more computer memory devices housed in the control system 140). The coronary sinus pressure data can be displayed by the graphical user interface 142 in a graph form so that a cardiologist or other user can readily monitor the trend of the coronary sinus pressure while the coronary sinus 20 is in an occluded condition and in a non-occluded condition. Optionally, the graphical user interface 142 of the control system 140 can also output a numeric pressure measurement on the screen so that the cardiologist can readily view a maximum coronary sinus pressure, a minimum coronary sinus pressure, or both. In alternative embodiments, the pressure sensor device 136 can be integrated into the housing of the control system 140 so that the third line 135 is a fluid-filled path leading up to the corresponding port 145, where the internal pressure sensor device (much like the device 136) samples the pressure measurements and outputs a signal indicative of the coronary sinus pressure.

Still referring to FIG. 2, the system 100 may include one or more ECG sensors 149 to output ECG signals to the control system 140. In this embodiment, the system 100 includes a pair of ECG sensor pads 149 that are adhered to the patient's skin proximate to the heart 10. The ECG sensors 149 are connected to the control system 140 via a cable that mates with a corresponding port 149 along the housing of the control system 140. As described in more detail below, the ECG data can be displayed by the graphical user interface 142 in a graph form so that a cardiologist or other user can readily monitor the patient's heart rate and other characteristics while the coronary sinus is in an occluded condition and in an non-occluded condition. Optionally, the graphical user interface 142 of the control system 140 can also output numeric heart rate data (based on the ECG sensor data on the screen so that the cardiologist can readily view the heart rate (e.g., in a unit of beats per minutes). The ECG sensor signals that are received by the control system 140 are also employed by the internal control circuit so as to properly time the start of the occlusion period (e.g., the start time at which the balloon device 122 is inflated) and the start of the non-occlusion period (e.g., the start time at which the balloon device 122 is deflated).

As shown in FIG. 2, the coronary sinus occlusion catheter 120 is delivered to the heart 10 via a venous system using any one of a number of venous access points. Such access points may be referred to as PICSO access points in some embodiments in which the coronary sinus occlusion catheter 120 is controlled to perform a PICSO procedure for at least a portion of the time in which the catheter 120 is positioned in the coronary sinus 20. For example, the guide member 110 and the distal tip portion 121 can be inserted into the venous system into an access point at a brachial vein, an access point at a subclavian vein, or at an access point at a jugular vein. From any of these access points, the guide member 110 can be advanced through the superior vena cava and into the right atrium 11. Preferably, the guide member 110 is steered into an ostial portion of the coronary sinus 20, and then the distal tip portion 121 of the catheter 120 is slidably advanced along the guide member 110 and into the coronary sinus 20 before the guide member 110 is backed out to remain in the right atrium 11. In another example, the guide member 110 and the distal tip portion 121 can be inserted into the venous system into an access point at a femoral vein. In this example, the guide member 110 can be advanced through the inferior vena cava and into the right atrium 11. As previously described, the distal tip portion 121 of the catheter 120 is slidably advanced along the guide member 110 and into the coronary sinus 20 before the guide member 110 is backed out to remain in the right atrium 11.

In some embodiments, the blockage 35 in the heart may be repaired or removed using a percutaneous coronary intervention (PCI) instrument such as an angioplasty balloon catheter, a stent delivery instrument, or the like. The PCI instrument may access the arterial system via any one of a number of PCI access points, as shown in FIG. 2. In some implementations, the PCI instrument can be inserted into the arterial system into an access point at a femoral artery, an access point at a radial artery, or an access point at a subclavian artery. Thus, as previously described, some embodiments of the system 100 may employ a PICSO access point into the venous system while a PCI access point is employed to insert a PCI instrument into the arterial system.

Referring now to FIG. 3, the catheter device 120 carries the balloon device 122 along its distal end portion. On its proximal end, the catheter 120 comprises a the hub portion 132, in which the proximal connection lines 133, 134, and 135 (not shown) are each connected with the respective lumens of the catheter 120 via a Y-connector 139. Alternatively, a multiple outlet for a plurality of feeds may be provided. One of the two proximal connection lines 133 is connected with the lumen (e.g., inflation lumen 158 (FIG. 5) serving to inflate and deflate the balloon 122 and carries a proximal connection piece 137 to which a fluid source may be connected. The other of the proximal connection lines 134 is connected with the lumen (balloon pressure-monitoring lumen 159 (FIG. 5) serving to measure the pressure internal to the balloon 122, and carries a proximal connection piece 137 which can be connected with an appropriate pressure measuring means. Finally, a Luer lock 138 may be guided out of the hub portion 132 for connection with the central lumen 125 (e.g., the pressure sensor lumen) of the catheter 120.

The distance between the tip of the catheter tip element 129 and the hub portion 132 is denoted by a and is, for instance, about one meter in order to enable the catheter to be introduced both via the jugular vein and via the femoral vein or the vein of the upper arm. A protective hose 118, which can be slipped over the catheter tip element 129 and the balloon 122 in the direction of arrow 119, is provided to protect the balloon 122 during the storage of the catheter 120.

From the detailed view according to FIG. 2, it is apparent that the balloon 122, in the inflated state, has a central, approximately cylindrical portion 152 which is adjoined by a conical portion 153 on either side, said conical portion 153 being each connected with the catheter shaft 155 via a collar-shaped end piece 154. In the inflated state, the diameter of the balloon 122 in the region of the cylindrical portion 152 may be, for instance, between about 12 mm and about 22 mm and, preferably, about 15 mm. The length b of the inflated portion of the balloon 122 may be, for instance, between about 20 mm and about 30 mm and, preferably, about 25 mm. By a marker band 156 positioned in the balloon 122 can carry an X-ray-compatible material so as to be rendered visible during a surgery by suitable imaging processes.

In accordance with some embodiments, the catheter shaft 155 may include a plurality of lumens extending from the hub portion 132 to the distal portion 121 (e.g., to the balloon 122 or to the tip element 129). As shown in the cross-sectional illustration according to FIG. 5, the catheter 120 has the central lumen 125 (e.g., the pressure sensor lumen in this embodiment) as well as two ring segment-shaped lumens 158 and 159. The ring segment-shaped lumen 158 (e.g., the inflation lumen in this embodiment), which extends over a larger central angle than the ring segment-shaped lumen 159 (e.g., the balloon-pressure monitoring lumen in this embodiment), thereby providing a larger arc length than the ring segment-shaped lumen 159. The inflation lumen 158 likewise communicates with the interior of the balloon 122 and serves to inflate and deflate the balloon 122. The balloon-pressure monitoring lumen 159 likewise communicates with the interior of the balloon 122 and serves to measure the pressure prevailing within the balloon 122.

From FIG. 9 (which illustrates a portion of the catheter 120 that is interior to the balloon 122 (with the balloon 122 removed from view), it is apparent that the lumens 158 and 159 are each in communication with the interior of the balloon via two openings 160 and 161 respectively provided in an axially offset manner. The use of at least two radial openings 160 and 161 into the interior of the balloon 122 can reduce the risk of the balloon prematurely covering all openings, particularly during collapsing, i.e. prior to the complete evacuation of the balloon, so that further evacuation would be rendered difficult or impossible. Between the mutually adjacent ends of the ring segment-shaped lumens 158 and 159, a lumen 157 having a circular cross section is arranged. Through the lumen 157, electric wirings, sensors or the like can be conducted. Also, in some embodiments, in the lumen 157, a stiffening wire (refer to wire 165 in FIG. 7) can be arranged in the region of the balloon 122, as will be described in more detail below. In addition or in the alternative, electric wirings, sensors or the like can also be conducted through the central lumen 157.

Accordingly, the lumens 125, 157, 158, and 159 of the catheter device 120 may have cross-sectional geometries differing from one another. For example, the inflation lumen 158 that serves to inflate and/or deflate the balloon may have a ring segment-shaped in cross section and arranged radially outside the central lumen 125. The second lumen 159 (e.g., the balloon pressure-monitoring lumen in this embodiment) may have a ring segment-shaped in cross section and arranged radially outside the central lumen 125, and the arc-determining angle is preferably smaller as compared to the ring segment-shaped inflation lumen 158. Due to the fact that the ring segment-shaped cross section of the inflation lumen 158 extends over a larger central angle than the ring segment-shaped cross section of the balloon pressure-monitoring lumen 159, a larger cross section is provided for the inflation lumen 158 and, at the same time, separate pressure measurements will be enabled. The ability to provide pressure measurements via the separate lumen 159, for instance, has the advantage that possible buckling under flexural load (or kinking) can be detected. Buckling can be reliably detected due to the different pressures measured in the inflation lumen 158 and in the separate lumen 159. In such circumstances, it is thus feasible to take the respective safety measurements, e.g. actuate a safety valve, in a prompt manner. From the cross-sectional illustration according to FIG. 6, it is apparent that a stiffening element 123 in the form of a hypotube surrounds the catheter shaft 155 is arranged at a distance c (FIG. 2) from the proximal end of the balloon 2. An example embodiment of the hypotube 123 is illustrated in FIG. 10. As shown in FIG. 7, the stiffening wire 165 made, for instance, of nitinol may be arranged in the lumen 157. The stiffening wire 165 may extend over the length of the balloon 122 so as to reduce the likelihood of the catheter shaft 155 buckling or otherwise deforming in the region in which it is surrounded by the balloon 122, on account of the balloon pressure exerting axial upsetting forces on the catheter shaft 155.

An example embodiment of the catheter tip element 129 is illustrated in detail in FIG. 7. There, the attachment of the collar 154 of the balloon 122 to the distal end of the catheter is, in particular, illustrated. The connection is realized via an interposed, distal filling member 166, whereby a material adhesion of the collar 154 with the catheter upon interposition of the filling member 166 is effected in this region by thermal bonding or gluing. A further marker band 167 can be arranged at a distance d (e.g., about 6.5 mm in this embodiment) from the distal opening 128 of the catheter tip element 129. The catheter tip element 129 is connected with the distal end of the catheter by the aid of a transition piece 169. It is apparent that the axial lumen 126 of the catheter tip element 129 is arranged immediately consecutive to the central lumen 125 of the catheter. The catheter tip element 129 comprises a portion conically tapering toward the distal opening 128 and including three openings 127 uniformly distributed about its periphery.

From the perspective illustration according to FIG. 8, it is apparent that the edge 162 of the distal opening 128 is rounded off in order to avoid damage to the vessel inner wall.

FIG. 10 depicts a hypotube 123 which comprises a helical line-shaped notch 163. It is apparent that the pitch of the helix 163 in the distal end portion 164 is smaller than in a more proximally located region 165. This results in a reduced flexural strength in the distal end portion 164 so as to enable the catheter to better follow the various curvatures of the body vessel during its introduction. In some embodiments, the pitch of the helix 163 at the distal end portion 164 relative to the pitch of the helix at the proximally located region 165 can be selected so that the flexural strength is a function of the length of the catheter leading up to the balloon Thus, as described herein, the catheter 120 can be configured to provide sufficient rigidity in order to reduce the likelihood the occlusion catheter device will slip back from the occluded position because of the counter-pressure in the occluded vessel. At the same time, the catheter 120 may provide sufficient flexibility in order to enable the catheter 120 to be safely pushed forward through blood vessel regions having small radii of curvature so as to be able to position the inflatable balloon 122 on the catheter 120 at the desired site of application (e.g., the coronary sinus 20).

In some embodiments, the flexural strength of the balloon catheter 120 is obtained by the stiffening element 123 that surrounds the catheter shaft 155. The stiffening element 123 also facilitates the advancement of the balloon catheter. In order reduce the likelihood of injuring the vessel during the advancement of the catheter, and to permit advancement in curved regions having small radii of curvature, the distal end portion 164 of the stiffening element 123 can be positioned adjacent to the proximal end of the balloon 122 and may provide a flexural strength that is reduced relative to the remaining portion of the stiffening element. Thus, a region of higher flexibility is deliberately formed at the distal end portion 164 of the stiffening element 123 so as to enable the adaptation to a curved course of the body vessel during the advancement of the catheter 120, while preferably maintaining the balloon-carrying, distal portion 121 of the catheter 120 in a generally parallel relationship with the longitudinal extension of the respective vessel in order to avoid injury to the vessel wall.

In particular embodiments, the stiffening element 123 may extend substantially over the entire portion of the catheter shaft 155 between the balloon 122 and the proximal hub portion 132. In a preferred embodiment, the distance c is provided between the distal end of the stiffening element 123 and the proximal end of the inflatable region of the balloon 122. In the embodiment described herein, the distance c is dimensioned such that, on the one hand, the catheter shaft will not buckle between the distal end of the stiffening tube and the balloon, which would be the case with too large a distance, and, on the other hand, the flexibility and suppleness will not be limited too much in this region, which would be the case with too short a distance, or no distance at all. In some preferred embodiments, the distance c is about 4-6 mm and, in particular, about 5 mm.

As shown in FIG. 10, the stiffening element 123 may be formed by a separate stainless-steel tube or also by at least one outer layer co-extruded with the catheter shaft 155 and made of a synthetic material differing from that of the catheter shaft 155. Alternatively, the stiffening element 123 may be formed by a nylon tissue or comprise such a tissue. In some embodiments, the portion of the stiffening element having a reduced flexural strength extends over a length of about 30-120 mm, preferably about 40-90 mm, from the distal end of the stiffening element.

According to a preferred configuration, the hypotube 123 can include at least one notch influencing the flexural strength. In the embodiment depicted in FIG. 10, the notch 163 preferably extends in a helical line-shaped manner, with the helical line or helix having a smaller pitch in the portion of reduced flexural strength of the hypotube than in the remaining portion. As described herein, further optimization is feasible in that the pitch of the helix 163 continuously increases in the portion of reduced flexural strength of the hypotube, departing from the distal end of the hypotube. Due to the continuously variable flexural strength of the hypotube in the mentioned end portion, buckling sites will be avoided.

In alternative embodiments, instead of a helical line-shaped notch 163, a plurality of notches offset in the axial direction may also be provided on the stiffening element. Each of the notches can extend over a partial circumference of the hypotube, with the flexural strength depending on the axial distance between the individual notches. A number of embodiments of the invention have been described. Nevertheless, it will be understood that various modifications may be made without departing from the scope of the invention. Accordingly, other embodiments are within the scope of the following claims.

What is claimed is:

1. An occlusion catheter device for intermittently occluding a coronary sinus, comprising:
    a catheter shaft that carries an inflatable balloon on a distal portion;
    a pressure sensor lumen extending centrally through the catheter shaft to a plurality of distal ports that are positioned distally of the balloon for communication with fluid in a coronary sinus;
    an inflation lumen to inflate and deflate the balloon;
    a stiffening element fixed to the catheter shaft and terminating proximally of an inflatable region of the balloon, the stiffening element having a distal end portion that has a flexural strength reduced relative to a remaining proximal portion of the stiffening element; and
    a balloon pressure-monitoring lumen to measure the pressure in the balloon, the balloon pressure-monitoring lumen having a ring segment-shape in cross section and being arranged offset from the pressure sensing lumen extending centrally through the catheter shaft, wherein the ring segment-shaped of the balloon pressure-monitoring lumen is smaller as compared to that of the inflation lumen;
    wherein the lumens extending through the catheter shaft have cross-sectional geometries differing from one another;
    wherein the inflation lumen has a ring segment-shaped in cross section and is arranged radially outside the pressure sensor lumen extending centrally through the catheter shaft; and
    wherein the inflation lumen and the balloon pressure-monitoring lumen are each connected with an interior of the balloon via at least two radial openings arranged to be offset in an axial direction of the catheter shaft.

2. The catheter device of claim 1, wherein the stiffening element is fixed on a same portion of the catheter shaft as the proximal end of the balloon.

3. The catheter device of claim 1, wherein a distance between the distal end of the stiffening element and the proximal end of the inflatable region of the balloon is between 4 mm and 6 mm.

4. A coronary sinus occlusion catheter device, comprising:
    a catheter shaft that carries an inflatable balloon on a distal portion;
    a pressure sensor lumen configured to be fluid-filled to sense pressure in the coronary sinus and extending centrally through the catheter shaft to a distal-facing port and a plurality of radially facing ports that are positioned distally of the balloon for communication with fluid in a coronary sinus;
    an inflation lumen to inflate and deflate the balloon; and
    a balloon pressure-monitoring lumen to measure the pressure in the balloon, the balloon pressure-monitoring lumen being different from and adjacent to the inflation lumen, wherein both the inflation lumen and the balloon pressure-monitoring lumen are in fluid communication with an interior of the balloon,
    wherein the pressure sensor lumen is fixed relative to the distal end of the balloon such that a longitudinal distance between the distal-facing port of the pressure sensor lumen and the distal end of the balloon is permanently greater than an axial length of an inflatable region of the inflatable balloon when the balloon is inflated; and
    wherein the inflation lumen and the balloon pressure-monitoring lumen are each connected with an interior of the balloon via at least two radial openings arranged to be offset in an axial direction of the catheter shaft.

5. The catheter device of claim 4, further comprising a stiffening element fixed to the catheter shaft and terminating proximally of the inflatable region of the balloon, the stiffening element having a distal end portion that has a flexural strength reduced relative to a remaining proximal portion of the stiffening element.

6. The catheter device of claim 4, further comprising a movable stiffening wire extending through a lumen of the catheter shaft in a region adjacent to the balloon, said lumen of the stiffening wire being axially offset from the pressure sensor lumen, said wire extending along a length of the balloon.

7. The catheter device of claim 6, further comprising a hypotube surrounding the catheter shaft to provide additional stiffening strength beyond said stiffening wire, the hypotube having a distal end portion that is positioned near to the proximal end of the balloon and has a flexural strength reduced relative to a remaining proximal portion of the hypotube.

8. The catheter device of claim 4, said longitudinal distance between the distal-facing port of the pressure sensor lumen the balloon is at least about 30 mm.

9. The catheter device of claim 4, wherein the longitudinal distance between the distal-facing port of the pressure sensor lumen and the distal end of the balloon is about 35 mm to about 45 mm.

10. The catheter device of claim 4, wherein said axial length of the inflatable balloon when the balloon is inflated is about 20 mm to about 30 mm.

\* \* \* \* \*